United States Patent [19]

Bouchaudon et al.

[11] B 4,013,565
[45] Mar. 22, 1977

[54] POLYOXETANES WHICH CAN BE USED IN PEPTIDE SYNTHESIS

[75] Inventors: Jean Bouchaudon, Morsang sur Orge; Guy Bourat, Bourg-la-Reine; Rodolphe Margraff, Ris Orangis, all of France

[73] Assignee: Rhone-Poulenc S.A., Paris, France

[22] Filed: July 31, 1974

[21] Appl. No.: 493,474

[44] Published under the second Trial Voluntary Protest Program on March 23, 1976 as document No. B 493,474.

Related U.S. Application Data

[62] Division of Ser. No. 335,177, Feb. 23, 1973, Pat. No. 3,847,868.

[30]    Foreign Application Priority Data

Feb. 28, 1972    France .................. 72.06696

[52] U.S. Cl. .......................................... 210/500 M
[51] Int. Cl.$^2$ .......................................... B01D 31/00
[58] Field of Search .......... 210/22, 23, 321, 500 M; 260/2 XA, 2.2

[56]          References Cited
         UNITED STATES PATENTS 3,459,687   8/1969   Bufton ............................ 260/2 XA

*Primary Examiner*—Frank A. Spear, Jr.
*Attorney, Agent, or Firm*—Stevens, Davis, Miller & Mosher

[57]            ABSTRACT

Polyoxetanes are provided which consist essentially of a plurality of units of the formula:

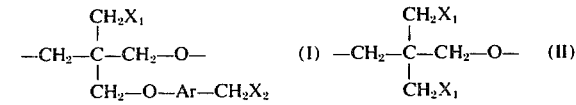

and optionally, of units of at least one of the formulae:

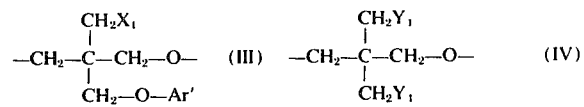

and

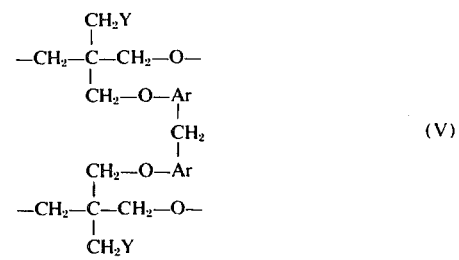

in which:
each of $X_1$ and $X_2$, which may be identical or different, represents a chlorine or bromine atom,
Y is as defined under $X_1$ or represents a radical of formula $-O-Ar-CH_2X_2$ or $-O-Ar'$,
each of the $Y_1$ radicals, which may be identical or different, represents a $-O-Ar'$ or $-O-Ar-CH_2X_2$ radical, Ar represents a divalent aromatic radical, the two free valencies of which are carried by carbon atoms of one or two aromatic benzene rings and
Ar' represents the radical $-ArH$, the units (I) to (V) being connected to one another via the oxygen atom with a free valency of one of the units and a methylene group with a free valency of the adjacent unit. These polyoxetanes, by reason of the fact that they swell very well in, for example, methylene chloride, are particularly suitable for use as the support in the preparation of peptides using solid phase synthesis.

12 Claims, No Drawings

POLYOXETANES WHICH CAN BE USED IN PEPTIDE SYNTHESIS

This is a division of application Ser. No. 335,177, filed Feb. 23, 1973, now U.S. Pat. No. 3,847,868.

This present invention relates to polyoxetanes which can be used as a substratum polymer for the synthesis of polypeptides.

According to the present invention there is provided a polyoxetane which comprises a plurality of units of the formula:

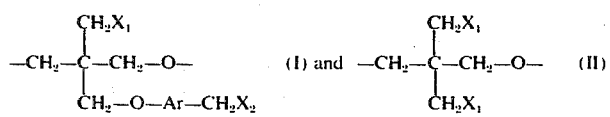

and, optionally, of units of at least one of the formulae:

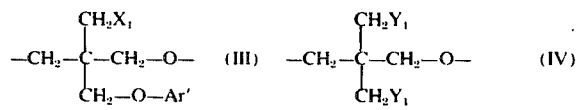

and

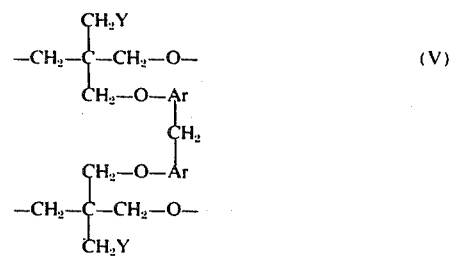

In these various units, the symbols may vary from one unit to the next. These symbols are defined as follows:

$X_1$ and $X_2$ represent a chlorine or bromine atom, Y represents $X_1$ or a radical of formula: —O—Ar—$CH_2X_2$ or —O—Ar', each of the $Y_1$ radicals represents a —O—Ar' radical or a —O—Ar—$CH_2X_2$ radical, Ar represents a divalent aromatic radical, the two free valencies of which are carried by carbon atoms belonging to one or two aromatic benzene rings, and Ar' is the radical —ArH.

The linking of the units (I) to (V) takes place between an oxygen atom with a free valency of one of the units and a methylene group with a free valency of an adjacent unit.

—Ar— is, more particularly, a radical of the formula:

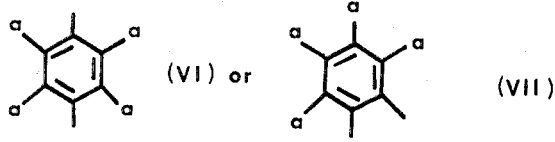

in which each of the a radicals, which may be identical or different, represents a hydrogen atom or a linear or branched alkyl, alkoxy or acyl radical, these radicals having generally less than 7 carbon atoms, or a nitro or nitrile group or a halogen atom, preferably chlorine or bromine, it being possible for at most half of the symbols a to have a meaning other than H, alkyl, alkoxy or acyl.

More specifically, as radicals Ar and Ar', there may be mentioned radicals such that H-Ar-OH and Ar'—OH represent meta-nitrophenol, o- or m-bromophenol, quaiacol, o- and m-cresol, o or m-iso- butylphenol, o or m-isopropylphenol, a xylenol, o- or m- chlorophenol, thymol or phenol itself.

The proportions of the various units are generally such that the number of —Ar$CH_2X_2$ groups, expressed in milliequivalents (meq) per gram of dry polymer, is between 0.5 and 4, and preferably between 1 and 3; the percentage by number of —$CH_2$—O—Ar - groups (including the —$CH_2$—O—Ar' groups, which are merely —$CH_2$—O—Ar—H) relative to the total number of the substituents of the polymer chains is generally between 1 and 60%, and preferably between 20 and 50%.

Furthermore, the degree of crosslinking, that is to say the percentage of units (V) relative to the other units, is generally less than 10%, and more particularly less than 1%.

The polyoxetanes according to the present invention are usually prepared by halomethylation of polyoxetanes, referred to hereafter as "intermediate phenoxylated polyoxetanes", comprising a plurality of units of formula (II) and of the formula:

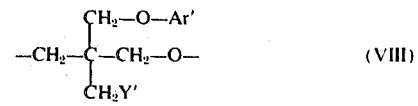

in which —Ar' is as defined above and Y' represents a chlorine or bromine atom or a —O—Ar' radical.

The halomethylation of the intermediate aryloxylated polyoxetanes can be carried out in a conventional manner for halomethylating aromatic rings, it being possible for the intermediate aryloxylated polyoxetane to be in the form of, for example, granules, shavings, a powder or a film which may optionally be screen-reinforced.

Suitable halomethylating agents are well known to those skilled in the art; they include methyl chloromethyl ether (also called monochloromethyl ether), ethyl chloromethyl ether and methyl bromomethyl ether, it being possible to prepare some of these ethers in situ, for example by reacting formaldehyde with hydrochloric or hydrobromic acid.

The halomethylation is generally carried out in the presence of a catalyst; for this purpose, Friedel-Crafts catalysts such as aluminum chloride, zinc chloride, antimony pentachloride, titanium tetrachloride, boron trifluoride or, preferably, tin tetrachloride can be employed.

The reaction temperature can vary within wide limits; it is usually between −10° and +50°C, and preferably between +10° and +30°C. The reaction is preferably carried out at atmospheric pressure, but it is also possible to work at higher or lower pressures. The halomethylation can take place with a halomethylating medium in the liquid phase or in the vapour phase. When the halomethylating medium is in the liquid phase, it is possible to carry out the reaction with or without a diluent. A liquid which is miscible with the reagents but is inert under the working conditions, for example an alkyl ether such as di-ethyl ether, is suitable as a diluent. It is generally preferred to carry out the reaction in the liquid phase, with a diluent and at atmospheric pressure.

The halomethylation reaction can be continued until the desired proportion of halomethyl groups have been attached to an aromatic ring; the reaction conditions, especially the temperature and the duration of the reaction, to be employed can, of course, be determined easily in each case by simple experiment. It should be noted that halomethylation of the units (VIII) can produce not only units such as (I) and (IV) with $Y_1$ representing $-O-Ar-CH_2X_2$ but also a certain degree of crosslinking as a result of secondary reactions, creating units (V). It should also be noted that, under the specified working conditions, halomethylation of the units (VIII) generally results in only one halomethyl group becoming attached per Ar' group undergoing reaction. It is however also possible for some Ar' groups to be substituted by more than one halomethyl group. It is believed, however, that the proportion of polyhalomethylated Ar' groups is relatively small and, for the purpose of simplification, such units have been excluded from the units given as forming the polymers of this invention, only average units being indicated. It is to be understood, however, that the presence of such units is not excluded from the polyoxetanes of this invention i.e. some of the $-Ar-CH_2X_2$ groups can be in the form $-Ar(CH_2X_2)_2$.

The intermediate aryloxylated polyethers are prepared advantageously from poly-3,3-bis-(halomethyl)-oxetane hereafter called PBMO) by replacing the halogen atoms by aryloxy radicals. This substitution, hereafter called "arloxylation", can be carried out easily by reacting PBMO with an alkali metal phenate of the formula Ar'—O—M, M being an alkali metal and preferably sodium or potassium, in an aprotic polar solvent, such as dimethylsulphoxide (DMSO), hexomethylphosphotriamide (HMPT), sulpholane, dimethylformamide, dimethylacetamide and tetramethylurea. The phenates which are derived from the phenols of the formula H—Ar—OH mentioned above are particularly suitable.

The starting PBMO generally has a molecular weight between 50,000 and 1,000,000, and preferably between 100,000 and 500,000.

The relative proportion of the reagents to be employed in order to achieve a particular proportion of aryloxy groups in the treated PBMO is preferably chosen by assuming quantitative yield during this aryloxylation; this is why the number of mols of phenate employed is usually between 1 and 60%, preferably between 20 and 50%, of the number of halomethyl groups present in the PBMO used.

The PBMO is employed at concentrations which are generally between 0.5 and 20% by weight, and preferably between 1 and 10%.

The temperature of the aryloxylation reaction is usually between 50° and 230°C, and preferably between 100° and 200°C. Of course, if a solvent which is unstable or volatile at high temperatures is used, the reaction should then be carried out, respectively, at a temperature below the decomposition temperature or at a pressure which is sufficient to keep the solvent in the liquid state.

The present invention also provides a process for the preparation of a peptide on a solid support in which the support (or substratum) consists, wholly or partially, of a polyoxetane according to the invention.

The technique of synthesising peptides on a solid support is known as "solid phase synthesis". Such a technique has been described, for example, in Advances in Enzymology, Robert B. Merrifield, 32, 221–296 (1969) and in French Specification No. 2,021,591. According to this technique an aminoacid possessing a protected amino group is attached to a gel of a nitrochloromethylated or chloromethylated polystyrene copolymer crosslinked with approximately 2% of divinyl-benzene, by carrying out the reaction according to the following equation:

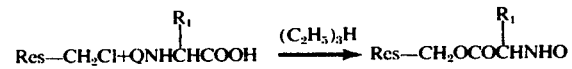

in which Res represents the base resin (or substratum), Q represents the group which protects the amine of the aminoacid, for example a benzyloxycarbonyl or t-butoxycarbonyl group, and $R_1$ represents the side chain of the first aminoacid.

After reaction, the protective group Q is removed and the next amino acid unit is added in accordance wtih the techniques used in peptide synthesis:

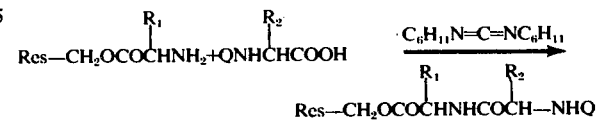

In this equation, $R_2$ represents the side chain of the second aminoacid and the other symbols are as defined above. The second stage is then repeated with a third blocked aminoacid and so on until the desired polypeptide structure is obtained. Finally, the complete polypeptide is isolated from the resin by ester hydrolysis techniques which do not affect the peptide bonds, for example by using hydrazine.

Amongst the properties which the substratum must possess are, simultaneously, insolubility in water and in the majority of organic solvents and a considerable capacity for swelling in certain organic solvents such as chloroform, dioxane and, especially methylene chloride. Since this swelling makes it easy for the reagents to reach the active sites of the substratum.

The polyoxetanes according to this invention are particularly useful as the substratum in such a synthesis of polypeptides precisely because of their excellent capacity for swelling in methylene chloride. This capacity for swelling is generally greater than that of the polymers or resins derived from polystyrene. Moreover, the $-O-Ar-$ groups assist the reactions for attaching aminoacids to the substratum; the use of Ar radicals substituted, for example, by nitro groups, also makes it possible to influence the labile nature of the bond between the substratum and the first aminoacid.

Because of the way in which they are prepared, the polyoxetanes according to the invention form a very good homogeneous material, especially from the point of view of the distribution of the mobile halogen atoms i.e. the halogen atoms of the halomethyl groups which are bonded exclusively to an aromatic radical and not to an aliphatic carbon atom.

The polyoxetanes according to the invention can also be used for the production of membranes. In the form of a membrane, particularly as a continuous strip, they make it possible to synthesise polypeptides continuously and automatically by successively passing the strip through baths of solvents or reagents: this technique advantageously replaces the known automatic techniques for solid phase synthesis which requires passing numerous solutions over a bed of resin with, preferably, use of combined feed and central remote control systems (see for example, U.S. Pat. No. 3,531,258).

The membranes based on polyoxetanes according to the invention may, if desired, be screen-reinforced, the term screen denoting a reinforcing support. For synthesising polypeptides, it is preferred to use screenreinforced membranes and, more especially, membranes which have been screen-reinforced with materials which are chemically inert towards halomethyl groups and are also chemically inert under the conditions of the peptide synthesis. The use of paper-like materials, for example polytetrafluoroethylene papers and glass fibre papers, as a screen makes it possible to stabilise the longitudinal or transverse dimensions of the membranes more effectively. The membranes according to the invention make it possible to obtain polypeptides having improved purity.

The production of screen-reinforced membranes is advantageously carried out by coating the screen with a solution of intermediate aryloxylated polymer, the halomethylation being carried out subsequently on the film thus produced. The term "coating" is used to denote, in general terms, bringing the screen into contact with a solution of intermediate aryloxylated polyoxetane followed by evaporating the solvent; impregnation or pouring can thus be used. The concentration of the solutions used naturally depends on the solvent; by carrying out several coatings, it is possible to attach variable amounts of polyoxetane to the screen. According to a preferred method for producing screen-reinforced membranes, coating is continued until the proportion of polyoxetane in the membrane is between 5 and 90%, and preferably between 20 and 70%. The halomethylation can then be carried out on the film under the same conditions as described above for the aryloxylated polyoxetane alone.

The following Examples further illustrate the present invention.

It has not been possible to measure the degree of crosslinking in all these Examples (accuracy of the measurements: 1%); the term "membrane" has been reserved for the products consisting of a screen coated with the polyoxetanes according to the invention; the products consisting of a screen coated with intermediate aryloxylated polymer are called "films".

The mobile chlorine atoms were measured by a) heating the sample under reflux for 3 hours in excess of a 5% solution of triethylamine in ethanol, followed by b) determination of the attached nitrogen.

EXAMPLE 1

A. Potassium phenate.

58 g of phenol are reacted, at ambient temperature (20°–25°C), with 300 cm$^3$ of a 2 M solution of potassium methylate in methanol, and then the methanol is evaporated.

B. Preparation of the intermediate phenoxylated polyoxetane.

The phenate is redissolved in 0.5 l of dimethylsulphoxide (DMSO) at 140°C. This solution is poured into a solution of 155 g of poly-3,3-bis-(chloromethyl)-oxetane (of molecular weight: 170,000) in 2 liters of DMSO heated to 140°C. The temperature is maintained, in an atmosphere of dry nitrogen and with stirring, for 1 hour 30 minutes.

The reaction mixture is then poured into 7 l of water; the product is salted out by means of sodium chloride, washed with hot water and methanol, redissolved in refluxing tetrahydrofurane (THF), filtered, reprecipitated from boiling water, rinsed with methanol and dried.

185 g of a solid are obtained which softens at about 105°C and contains 26.2% by weight of chlorine, representing a degree of phenoxylation of 30%.

C. Conversion to a screen-reinforced film.

A sheet of paper made of glass fibres having the following characteristics:

| | |
|---|---|
| thickness: | 0.25 mm |
| porosity: | 500% (that is to say 100 g of paper absorb 500 g of water) and |
| weight (g per m$^2$): | 52.5 | is immersed for 15 minutes in a solution of the polyoxetane prepared under (B) in tetrahydrofurane of concentration 60 g/l.

The product is dried for 1 hour and then this sequence of operations is repeated. A screen-reinforced film containing intermediate phenoxylated polyoxetane is thus obtained.

D. Chloromethylation.

The film prepared under (C) is immersed for 20 hours at 20°C in the following mixture:

| | |
|---|---|
| diethyl ether: | 900 cm$^3$ |
| monochloromethyl ether: | 100 cm$^3$ |
| tin tetrachloride: | 10 cm$^3$. |

The membrane thus obtained is washed with diethyl ether and dried at 20°C at 30 mm Hg.

A white membrane is thus obtained having the following characteristics: density: 110.5 g/m$^2$; proportion of mobile chlorine i.e. chlorine atoms which belong to chloromethyl groups attached to aromatic rings): 1.14 meg/g, corresponding to approximately 0.125 mol/m$^2$.

The proportion of polyoxethane in the membrane is 52.5% by weight; the polyoxethane is composed essentially of units of formula:

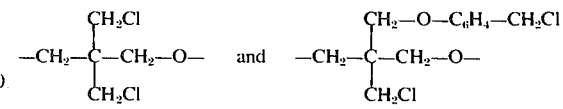

as well as a few units of formula:

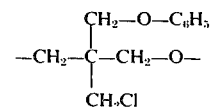

E. Esterification by N-o-nitrophenylsulphenyl-D,L-valine (abbreviated to NPS-D-,L-valine) of the formula

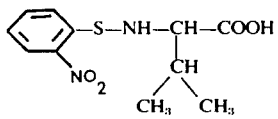
(the D, L-form)

Five esterification experiments are carried out in five different solvents, the common method of procedure being as follows:

438 mg of the membrane prepared under D) (0.5 mmol of mobile chlorine) are immersed in a solution of 135 mg (0.5 mmol) of NPS-D,L-valine in 25 cm$^3$ of solvent. After 10 minutes, 0.063 cm$^3$ of triethylamine (0.45 mmol) is added and the mixture is heated for 24 hours at 90°C in an atmosphere of dry nitrogen. The membrane is then washed first with dioxane and then with methylene chloride.

The protective group NPS-($NO_2$-$C_6$-$H_4$-S-) is then removed by immersing the membrane in a 0.2 N solution of anhydrous HCl in methylene chloride, at 20°C; the membrane is rinsed with methylene chloride, neutralised by a 5% solution of $(C_2H_5)_3N$ in methylene chloride, and washed again with methylene chloride followed by, successively, dioxane and methanol. A flexible membrane is thus obtained to which valine is attached via its acid group.

F. Determination of the aminoacid attached.

In order to determine the amount of valine attached, the valine is liberated by treating the membrane, at 100°C, in a sealed tube, for 24 hours, with a mixture of equal volumes of dioxane and 6 N aqueous hydrochloric acid, and then the valine in solution is measured by means of a "Technicon" automatic analyser which operates by chromatography on an ion exchange resin in accordance with the method of Moore and Stein.

The following results were obtained for each of the five solvents used during the esterification:

| Solvent used | Amount of valine attached in millimol per g of membrane |
|---|---|
| absolute ethanol | 0.28 |
| 90/10 mixture by volume of 1,2-dichloroethane and absolute ethanol | 0.20 |
| dimethylformamide | 0.25 |
| acetonitrile | 0.33 |
| ethyl acetate | 0.20 |

EXAMPLE 2

A and B. The procedure of Example 1, paragraphs (A) and (B), is followed, with the following changes: 76 g of phenol, instead of 58 g, and 400 cm$^3$ of methylate solution, instead of 300 cm$^3$. The period for which the methylate-4-poly-3,3-bis-chloromethyl-oxetane mixture is heated is 3 hours instead of 1 hour 30 minutes.

A phenoxylated polyoxetane with a degree of phenoxylation of 40% is thus obtained.

C. The procedure of Example 1, paragraph (C) is followed, using a solution of the phenoxylated polyoxetane containing 100 g/l (instead of 60 g/l).

D. The procedure of Example 1, paragraph D) is followed.

A white membrane having the following characteristics is thus obtained:

| | |
|---|---|
| density: | 105 g/m$^2$ |
| proportion of polymer: | 50% |
| proportion of mobile chlorine: | 1.25 meq/g. |

The polyoxetane consists essentially of units of the same formula as the polyoxetane units of Example 1.

E. This membrane is esterified under the conditions of Example 1, paragraph (E) in an acetonitrile medium, by means of NPS-L-phenylalanine of the formula:

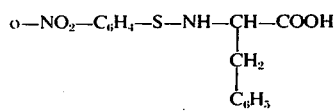

the molar ratios employed being the same as in Example 1, and then the protective NPS group is removed as in Example 1.

A flexible membrane is thus obtained to which L-phenylalanine is attached via its acid group.

F. Determination of the aminoacid.

In order to determine the amount of phenylalanine attached, the latter is liberated in the same way as the valine of Example 1 and it is determined in accordance with the technique mentioned in Example 1.

There is found to be 0.94 mmol of L-phenylalanine per g of dry membrane.

EXAMPLE 3

A and B. The procedure of Example 1, paragraphs (A) and (B), is followed.

C. The procedure of Example 1, paragraph (C) is followed, but 4 coatings are carried out instead of 2.

D. The procedure of Example 1, paragraph D) is followed.

A white membrane having the following characteristics is thus obtained:

| | |
|---|---|
| density: | 179 g/m$^2$ |
| proportion of polymer | 65.8% |
| proportion of mobile chlorine: | 1.43 meq/g. |

The polyoxetane consists essentially of units of the same formula as those of the polyoxetane of Example 1.

E. Esterification by benzyloxycarbonyl-N-glycine (BZN-glycine) of the formula: $C_6H_5$—$CH_2$—O—CO—NH—$CH_2$—COOH.

685 mg of membrane as prepared under D) (corresponding to 0.98 mmol of mobile chlorine) are heated under reflux for 24 hours in a solution prepared from 1 mmol of BZN-glycine, 0.126 cm$^3$ of triethylamine and 60 cm$^3$ of a 90/10 by volume dichloroethane/ethanol mixture.

The membrane is then washed with ethanol, followed by methylene chloride, followed by acetic acid.

F. Determination of the aminoacid attached.

The ester bond is hydrolysed as in Example 1, paragraph (F), and the glycine is determined in accordance with the technique indicated in Example 1.

0.45 meg of glycine per g of dry membrane is measured.

EXAMPLE 4

A and B. The procedure of Example 1, paragraphs (A) and (B) is followed.

C. The procedure of Example 1, paragraph (C) is followed, but only one coating is carried out instead of two. D. The procedure of Example 1, paragraph (D) is

| Operation or group of operations | Reagent (or solvent) | Number of operations | Volume of reagent in cm³ per operation | Duration of stirring per operation in minutes (unless otherwise stated) | Nature or purpose of the operation |
| --- | --- | --- | --- | --- | --- |
| 1 | acetic acid | 3 | 60 | 3 | washing |
| 2 | N solution of HCl in CH₃COOH | 1 | 60 | 30 | removal of the group protecting the amino radical in the α-position |
| 3a | acetic acid | 3 | 60 | 3 | washing |
| 3b | ethanol | 3 | 60 | 3 | washing |
| 3c | chloroform | 3 | 60 | 3 | washing |
| 4 | CHCl₃/(C₂H₅)₃N mixture; 9/1 by volume | 1 | 60 | 20 | neutralisation |
| 5a | chloroform | 3 | 60 | 3 | washing |
| 5b | ethanol | 3 | 60 | 3 | washing |
| 5c | methylene chloride | 3 | 60 | 3 | washing |
| 6a | aminoacid to be attached, dissolved in methylene chloride | 1 | 60 | 10 | mixing |
| 6b | 2.06 g of dicyclohexylcarbodi-imide dissolved in 60 cm³ of methylene chloride | 1 | 15 | 17 hrs. | condensation (attachment of the aminoacid) |
| 7a | methylene chloride | 3 | 60 | 3 | washing |
| 7b | ethanol | 3 | 60 | 3 | washing | followed.

A white membrane having the following characteristics is thus obtained:

density: 67 g/m²
proportion of polymer: 21.5%
proportion of mobile chlorine: 0.46 meq/g.

The polyoxetane consists essentially of units having the same formula as those of Example 1.

E. Attachment of N-α-t-butoxycarbonyl-N-γ-benzyloxy-carbonyl-L-α,γ-diamino-butyric acid.

2.8 cm³ of triethylamine are added to a solution of 7.05 g of N-α-t-butoxycarbonyl-N-γ-benzyloxycarbonyl-L-α-γ-diamino-butyric acid in 100 cm³ of ethanol. The mixture is stirred for 3 minutes at 20°C and then concentrated at 50°C under reduced pressure (20 mm of mercury). The oil obtained is dissolved in a mixture of 50 cm³ of ethanol and 450 cm³ of dichloroethane.

4.28 g of membrane as prepared under (D) are added to this solution.

This mixture is stirred for 54 hours at the reflux temperature, filtered, and then washed 3 times using, on each occasion, 70 cm³ of dichloroethane followed by 70 cm³ of ethanol. The produce is dried at 20°C under reduced pressure (0.3 mm of mercury) and 5.1 g of "intermediate polymer-blocked aminoacid " or N-α-t-butyoxycarbonyl-N-γ-benzyloxycarbonyl-L-α,γ-diamino-butyryl-"polymer" are thus obtained, that is to say a polymer or substratum to which N-α-t-butoxycarbonyl-N-γ-benzyloxy-carbonyl-L-α,γ-diaminobutyryl radicals are attached. The proportion of N-α-t-butoxycarbonyl-N-γ-benzyloxy-carbonyl-L-α,γ-diamino-butyric acid in this polymer is equal to 0.15 mmol/g.

F. Attachment of N-t-butoxycarbonyl-L-threonine.

The second aminoacid (N-t-butoxycarbonyl-L-threonine) is attached by fixing the latter to 5 g of "intermediate polymer-blocked aminoacid" prepared under (E) (which contains 0.75 mmol of blocked aminoacid), the operations being carried out as indicated in Table (I) at 20°C; this is followed by filtering off except between operations 6a and 6b. In the course of operation 6a of Table I, a solution of 2.19 g of N-t-butoxycarbonyl-L-threonine in 60 cm³ of methylene chloride is used.

G. Attachment of N-α-t-butoxycarbonyl-N-γ-benzyloxy-carbonyl-L-α,γ-diamino-butyric acid.

This blocked aminoacid is attached to the polymer obtained at the end of paragraph (F).

The same procedure is used as in paragraph (F) and the associated Table (I), with the change that during operation 6a a solution prepared from 60 cm³ of methylene chloride and 3.52 g of N-α-t-butoxycarbonyl-N-γ-benzyloxycarbonyl-L-α,γ-diamino-butyric acid is used.

H. Attachment of L-6-methyl-octanoic acid prepared according to K. VOLGER et al., Helv. Chim. Acta, 43, 279 (1960).

This acid is attached to the polymer obtained at the end of the paragraph (G).

The same procedure is used as in paragraph (G) with the change that during operation 6a a solution of 1.58 g of L-6-methyl-octanoic acid in 60 cm³ of methylene chloride is used.

N-α-L-6-Methyl-octanoyl-N-γ-benzyloxycarbonyl-L-α,γ-diamino-butyryl-L-threnoyl-N-γ-benzyloxycarbonyl-L-α, γ-diamino-butyryl -"polymer" is thus obtained.

J. Isolation of the peptide thus synthesised, in the form of the hydrazide.

The polymer prepared in paragraph (H) is introduced into 100 cm³ of a solution of dimethylformamide containing 20% (by volume) of hydrazine hydrate. The mixture is allowed to react, with stirring, for 17 hours at 20°C. It is filtered, washed with dimethylformamide and concentrated to dryness (at 55°C 0.3 mm Hg); the residue is taken up again in 80 cm³ of water, left to stand for 1 hour at 4°C and filtered; the insoluble material is washed with water and then with methanol and ether. After drying (20°C; 0.3 mm of mercury), 355 mg of N-α-L-6methyl-octanoyl-N-γbenzyloxycarbonyl-lα,γ-diaminobutyryl-L-threonyl-N-γ-benzyloxycarbonyl-L-α,γ-diaminobutyryl-hydrazide are obtained.

| Analysis: | | | |
|---|---|---|---|
| calculated: | C:59.9; | H 7.47; | N: 13.21 |
| found: | C:60.2; | H 7.65; | N: 13.7. |

We claim:

1. A membrane consisting of a polyoxetane which consists of essentially of a plurality of units of the formula:

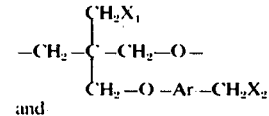 (I) 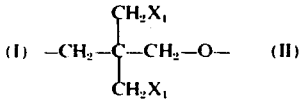 (II)

and and, optionally, of units of at least one of the formulae:

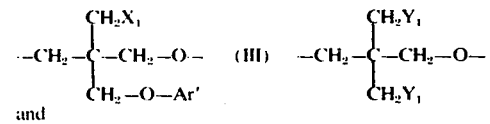 (III) (IV)

and

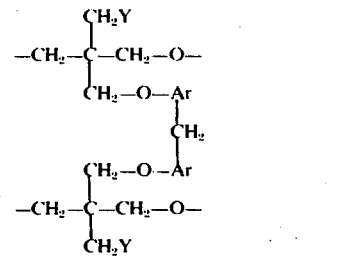 (V)

in which:
each of $X_1$ and $X_2$, which may be identical or different, represents a chlorine or bromine atom,
Y as defined under $X_1$ or represents a radical of formula: $-O-Ar-CH_2X_2$ or $-O-Ar'$,
each of the $Y_1$ radicals, which may be identical or different, represents a $-O-Ar'$ or $-O-Ar-CH_2X_2$ radical,
Ar represents a divalent aromatic radical, the two free valencies of which are carried by carbon atoms of one or two aromatic benzene rings and
Ar' represents the radical $-ARH$,
the units (I) to (V) being connected to one another via the oxygen atom with a free valency of one of the units and a methylene group with a free valency of the adjacent unit, and a screen reinforcement.

2. A screen-reinforced membrane according to claim 1 in which the screen is made of a material which is chemically inert towards compounds possessing halomethyl groups and towards the reagents used in peptide syntheses.

3. A membrane according to claim 2 in which the screen is made of glass fibre paper or polytetra-fluoroethylene paper.

4. A membrane according to claim 1 in which the polyoxetane is present in an amount between 5 and 90% by weight.

5. A membrane according to claim 4 in which the polyoxetane is present in an amount between 20 and 70% by weight.

6. A membrane according to claim 1 in which $-Ar-$ represents a radical of the formula:

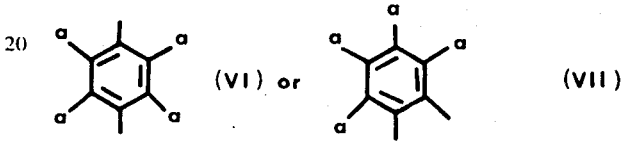

in which each of the a radicals, which may be identical or different, represents a hydrogen atom or a linear or branched alkyl, alkoxy or acyl radical or a nitro or nitrile group or a halogen atom, with the proviso that at most half of the radicals are other than hydrogen, alkyl, alkoxy or acyl.

7. A membrane according to claim 6 in which a represents an alkyl, alkoxy or acyl radical with less than 7 carbon atoms or a chlorine or bromine atom.

8. A membrane according to claim 1 in which $-Ar-$ and $-Ar'$ are such that $H-Ar-OH$ and $Ar'-OH$ represent meta-nitrophenol, o- or m-bromophenol, guaiacol, o- or m-cresol, o- or m-isobutylphenol, o- or m-isopropyl-phenol, a xylenol, o- or m-chlorophenol, thymol or phenol.

9. A membrane according to claim 1 in which the number of groups $-ArCH_2X_2$, expressed in milliequivalents (meg) per gram of dry polymer, is between 0.5 and 4.

10. A membrane according to claim 9 in which the number of $-ArCH_2X_2$ groups, expressed in milliequivalents per gram of dry polymer is between 1 and 3.

11. A polyoxetane according to claim 1 in which the percentage by number of groups $-CH_2-O-Ar-$ (including the groups $-CH_2-O-Ar'$) relative to the total number of substituents of the polymer chain is between 1 and 60%.

12. A polyoxetane according to claim 11 in which the percentage by number of groups $-CH_2-O-Ar-$ relative to the total number of substituents of the polymer chain is between 20 and 50%.

* * * * *